United States Patent
Ghosh et al.

(10) Patent No.: US 9,452,993 B2
(45) Date of Patent: Sep. 27, 2016

(54) PROCESS FOR IMPROVED SEAWEED BIOMASS CONVERSION FOR FUEL INTERMEDIATES, AGRICULTURAL NUTRIENTS AND FRESH WATER

(71) Applicant: Council of Scientific & Industrial Research, New Delhi (IN)

(72) Inventors: Pushpito Kumar Ghosh, Gujarat (IN); Dibyendu Mondal, Gujarat (IN); Pratyush Maiti, Gujarat (IN); Kamalesh Prasad, Gujarat (IN); Subarna Maiti, Gujarat (IN); Bharti Gunvantray Shah, Gujarat (IN); Arup Kumar Siddhanta, Gujarat (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/421,093

(22) PCT Filed: Aug. 12, 2013

(86) PCT No.: PCT/IN2013/000493
§ 371 (c)(1),
(2) Date: Feb. 11, 2015

(87) PCT Pub. No.: WO2014/027368
PCT Pub. Date: Feb. 20, 2014

(65) Prior Publication Data
US 2015/0232438 A1   Aug. 20, 2015

(30) Foreign Application Priority Data
Aug. 11, 2012  (IN) ............................ 1789/DEL/2012

(51) Int. Cl.
| | | |
|---|---|---|
| C05D 1/00 | (2006.01) |
| C07D 307/46 | (2006.01) |
| C07H 3/02 | (2006.01) |
| C07C 51/31 | (2006.01) |
| C02F 1/04 | (2006.01) |
| C02F 1/28 | (2006.01) |

(52) U.S. Cl.
CPC ............... *C07D 307/46* (2013.01); *C02F 1/04* (2013.01); *C02F 1/283* (2013.01); *C05D 1/00* (2013.01); *C07C 51/31* (2013.01); *C07H 3/02* (2013.01); *C02F 2303/02* (2013.01)

(58) Field of Classification Search
CPC ...... C07D 307/46; C07H 3/02; C07C 51/31; C05D 1/00; C02F 1/04; C02F 1/283; C02F 2203/02
USPC ................ 71/61; 203/29; 536/128; 549/408; 562/609
See application file for complete search history.

(56) References Cited

U.S. PATENT DOCUMENTS

| | | |
|---|---|---|
| 6,893,479 B2 | 5/2005 | Eswaran et al. |
| 8,399,688 B2 | 3/2013 | Dumesic et al. |

FOREIGN PATENT DOCUMENTS

| | | |
|---|---|---|
| WO | WO-2004/016656 A1 | 2/2004 |
| WO | WO-2010/021621 A1 | 2/2010 |

OTHER PUBLICATIONS

Khambhaty, Yasmin et al., "*Kappaphycus alvarezii* as a source of bioethanol," Bioresource Technology, vol. 103, No. 1, Oct. 4, 2011, pp. 180-185, XP028120860.

(Continued)

*Primary Examiner* — Jennifer A Smith
(74) *Attorney, Agent, or Firm* — Foley & Lardner LLP

(57) ABSTRACT

The invention relates to an integrated process for the production of 5-hydroxymethyl furfural (HMF), $K_2SO_4$, levulinic acid and formic acid from κ-carrageenan, the latter being obtained from fresh *Kappaphycus alvarezii* seaweed biomass after expelling the juice. $Mg(HSO_4)_2$ was used in HMF synthesis, with co-production of galactose. The aqueous stream after HMF extraction was treated with the seaweed juice which process facilitated recovery of $K_2SO_4$ in pure form. The galactose may be utilised for synthesis of levulinic acid and formic acid before or after $K_2SO_4$ recovery or, alternatively, utilised for other purposes. Catalysts required in the synthetic reactions are generated in the process itself while the process energy required is met out of additional supplies of the seaweed biomass which is subjected to combustion/gasification.

15 Claims, 2 Drawing Sheets

(56) References Cited

OTHER PUBLICATIONS

Meinita, Maria Dyah Nur et al., "Comparison of sulfuric and hydrochloric acids as catalysts in hydrolysis of *Kappaphycus alvarezii* (cottonii)," Bioprocess and Biosystems Engineering, vol. 35, No. 1-2, Sep. 10, 2011, pp. 123-128, XP019997287.

Mondal, D. et al., "Fuel intermediates, agricultural nutrients and pure water from *Kappaphycus alvarezii* seaweed," RSC Advances, vol. 3, No. 39, Jul. 31, 2013, pp. 17989-17997, XP055098346.

Ragauskas, A.J., et al., "The path forward for biofuels and biomaterials," Science, vol. 311, No. 5760, Jan. 27, 2006, pp. 484-489, XP002491106.

Written Opinion and International Search Report dated Feb. 7, 2014 issued in Application No. PCT/IN2013/000493.

PROCESS FOR IMPROVED SEAWEED BIOMASS CONVERSION FOR FUEL INTERMEDIATES, AGRICULTURAL NUTRIENTS AND FRESH WATER

CROSS REFERENCE TO RELATED APPLICATIONS

This application is the National Phase of PCT/IN 2013/000493, filed Aug. 12, 2013, which claims priority to Indian Application No. 1789/DEL/2012, filed Aug. 11, 2012.

The following specification particularly describes the nature of the invention and the manner in which it is to be performed:

FIELD OF THE INVENTION

The present invention relates to an improved process for the utilization of granules of *Kappaphycus alvarezii* obtained after expelling sap from the fresh seaweed. Particularly, present invention relates to its improved conversion for fuel intermediates, agricultural nutrients (fertilizers) and fresh water. More particularly, the invention relates to production of hydroxymethyl furfural (HMF) and levulinic acid/formic acid combination in step-wise manner besides obtaining potassium sulphate in pure form and drawing on the seaweed biomass itself for process energy requirement.

BACKGROUND AND PRIOR ART OF THE INVENTION

Reference may be made to the patent entitled "Integrated method for production of carrageenan and liquid fertilizer from fresh seaweeds" (Eswaran et al. U.S. Pat. No. 6,893,479). The patent teaches the production of carrageenan-rich granule by expelling sap from fresh *Kappaphycus alvarezii* Reference may be made to the patent application entitled "A process for integrated production of ethanol and seaweed sap from *Kappaphycus alvarezii* (Mody et al. Patent Filed Indian Application No. 1839/DEL/2009 dated Jul. 9, 2009; WO 2011/027360A1, dated Oct. 3, 2011.) which teaches the production of ethanol from the granules of *Kappaphycus alvarezii*.

Reference may also be made to the paper entitled "*Kappaphycus alvarezii* as a source of bioethanol" (Khambaty et al. Bioresource Technology, Volume 103, Issue 1, January 2012, 180-185) which provides details of the process of ethanol production and indicates that only a part of the total sugar obtained is reducing sugar and that it is the latter which yields ethanol. No mention is made of the other constituents.

Reference may be made to the work by Maria Dyah Nur Meinita, Yong-Ki Hong and Gwi-Taek Jeong entitled "Comparison of sulfuric and hydrochloric acids as catalysts in hydrolysis of *Kappaphycus alvarezii (cottonii)*" (Bioprocess Biosyst Eng (2012) 35:123-128). In this work hydroxyl methyl furfural and levulinic acid were obtained as by-products under the different conditions of hydrolysis.

Reference may be made to the paper entitled "Detoxification of acidic catalyzed hydrolysate of *Kappaphycus alvarezii(cottonii)*" (Bioprocess Biosyst Eng (2012) 35:93-98). In this article the authors have studied the effect of HMF and levulinic acid on ethanol fermentation, and they tried to remove these fermentation inhibitors from the hydrolysate of *K. alvarezii*.

Reference may be made to the review article entitled "The Path Forward for Biofuel and Biomaterials" (Science, volume 311, 27 Jan. 2006, 484-489). In which, the authors have pointed out the inefficiency of bioethanol production from biomass and suggest that HMF or levulinic acid pathway may provide better solutions for biofuel production.

Reference may be made to Korean Patent Application (KR20110051865 (A) dated 2011 May 18) entitled "Method of Preparing 5-Hydroxymethylfurfural from Seaweeds".

Reference may be made to CN10261752A which teaches production HMF from biomass using biphasic system and using acid salts of sulphuric acid and sulphuric acid metal salts as catalyst.

Reference may be made to CN102617523A wherein a method for preparing 5-hydroxymethylfurfural by hydrothermally decomposing wood fibers is disclosed. Reference may be made to U.S. Pat. No. 8,399,688 wherein, a method of making levulinic acid (LA), furfural, or gamma-valerolactone (GVL) from C5 and C6 carbohydrates in mono- and biphasic systems using gamma-valerolactone as a solvent is disclosed.

Reference may be made to the work entitled "Preparation of hydroxymethylfurfural and levulinic acid from phylophora" (Source: Zhurnal Prikladnoi Khimii (Sankt-Peterburg, Russian Federation), Volume: 44, Issue: 3, Pages: 697-9, Journal, 1971). The reported yields of HMF and levulinic acid were 8.75% and 14.75%, respectively.

Reference may be made to the work done by T. Thananatthanachon and Thomas B. Rauchfuss in the article entitled "Efficient Production of the Liquid Fuel 2,5-Dimethylfuran from fructose using formic acid as a reagent" (Angew. Chem. Int. Ed. 2010, 49, 6616-6618).

Reference may be made to the work by Li Deng et al in the paper entitled "Catalytic Conversion of Biomass-Derived Carbohydrates into ••Valerolactone without Using an External $H_2$ Supply" (Angew. Chem. Int. Ed. 2009, 48, 6529-6532) and the references included therein.

Reference may be made to the work by B. Kim et al., where they have described a method for the production of a mixture of HMF and Levulinic acid from agar using an ionic liquid and a chromium salt besides a solid acid catalyst. (*ChemSusChem*, 2010, 3, 1273-1275).

Reference may be made to the work by Ryan et al., wherein the extraction of monosaccharides from aqueous phase to organic phase is disclosed. (PNAS, 2002, 99, 4863-4866).

OBJECTS OF THE INVENTION

The main object of the present invention is to provide a process for improved seaweed biomass conversion for fuel intermediates, agri-nutrients (fertilizer) and fresh water.

Another object of the present invention is to provide fuel intermediates, agri-nutrients and fresh water from fresh biomass of *Kappaphycus alvarezii* in sustainable and integrated manner.

Another object of the present invention is to use the seaweed juice and residual granular biomass as the two raw materials.

Another object of the present invention is to convert the granular biomass into hydroxymethyl furfural (HMF), galactose and potassium sulphate.

Another object of the present invention is to utilize magnesium bisulphate as catalyst in synthesis of HMF and galactose.

Another object of the present invention is to recover pure galactose or convert it into ethanol by known methods or convert it into levulinic acid and formic acid also by known methods.

Another object of the present invention is to utilize seaweed juice and spent aqueous stream for recovery of potassium sulphate in pure form.

Another object is to recover fresh water.

Another object of the present invention is to make use of the granular biomass as source of process energy.

Another object of the present invention is to generate catalysts required in the processes from the integrated process itself.

Another object of the present invention is to recover glaserite-type fertilizer from combustion/gasification of granule as a second potash fertilizer.

Another object of the present invention is to use the surplus juice as a third agri-nutrient as already reported in the prior art.

SUMMARY OF THE INVENTION

Figure 1:
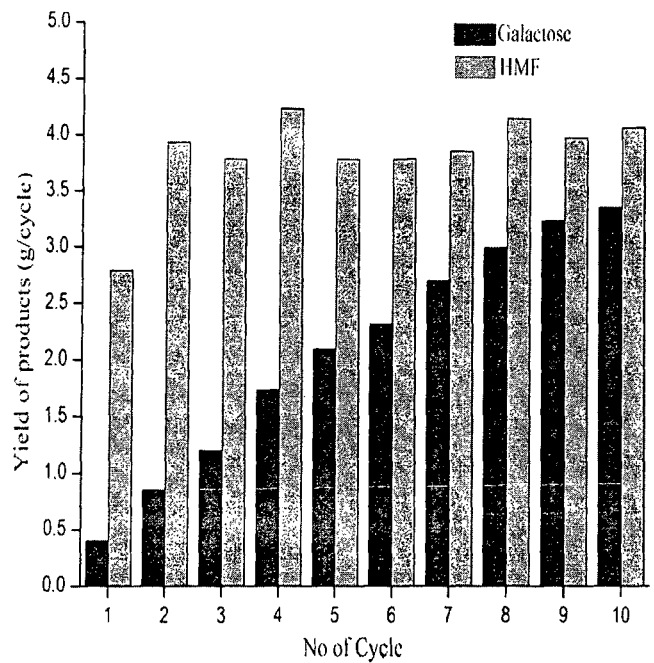
FIG. 1 represents bar diagram of HMF and galactose yield for 10 cycles with reuse 95 of acidic aqueous phase (10 g κ-carrageenan was added in each cycle, catalyst was 200 mL 0.48 M Mg(HSO4)2 and reaction condition was 105° C. for 1 h in autoclave (standard deviation: 0.16 g for cycles 3-10).

Accordingly, present invention provides an integrated process for the production of fuel intermediates, agri-nutrients and potable water from the fresh biomass of *Kappaphycus alvarezii* seaweed comprising the steps of:
  i. expelling of the seaweed juice from the fresh biomass by the known method of mechanically shearing of the seaweed and filtering the resultant slurry to obtain residual biomass and sea weed juice;
  ii. extracting pristine κ-carrageenan from residual biomass as obtained in step (i) using seawater under autoclaved condition at temperature range of 105° C.-120° C. at pressure in the range of 25 to 35 kPa for period in the range of 50 to 70 minute followed by precipitating with Isopropyl alcohol (IPA) to obtain pristine κ-carrageenan;
  iii. treating 5-10% (w/v) pristine κ-carrageenan as obtained in step (ii) with aqueous acid catalyst under autoclave condition at temperature in the range of 100-110° C. for period in the range of 1-3 hour to obtain 5-hydroxymethyl furfural (HMF), galactose and additional amount of bisulphate as potassium bisulphate generated from the substrate itself;
  iv. extracting the HMF as obtained in step (iii) in pure form with organic solvent and thereafter neutralizing the generated bisulphate in aqueous phase with magnesium hydroxide;
  v. charging fresh lot of κ-carrageenan into the aqueous phase and repeating the process of step (iii) and continuing in this manner over several cycles using the same organic layer or fresh solvent for HMF extraction;
  vi. neutralizing the aqueous layer to neutral pH with magnesium hydroxide;
  vii. adding seaweed juice to shift the equilibrium of the composition of the aqueous phase from schoenite to potassium sulphate and carrying out thermal distillation to recover potassium sulphate in pure form;
  viii. recovering galactose in pure form by known method of concentration and crystallisation or converting it into ethanol by known methods or treating the aqueous phase with acid catalyst under autoclave condition to convert galactose into levulinic acid and formic acid;
  ix neutralizing the spent aqueous layer, recovering magnesium hydroxide and thereafter fortifying the surplus juice with the nutrient rich aqueous stream.

In an embodiment of the present invention, the yield of pristine κ-carrageenan is 45-55% (w/w) from filtrate whereas the yield of insoluble residue useful as thermal energy source is 30-35% (w/w) and having calorific value 14-15 MJ/kg.

In another embodiment of the present invention, the acid catalyst used is selected from $Mg(HSO_4)_2$ or $H_2SO_4$ preferably $Mg(HSO_4)_2$.

In yet another embodiment of the present invention, concentration of magnesium bisulphate catalyst is in the range of 0.33-0.63 M preferably 0.46-0.50 M.

In yet another embodiment of the present invention, 5-hydroxymethyl furfural (HMF) obtained exhibit carbon utilization efficiency in the range of 25-70% preferably 55-65% with respect to carbon amount in substrate taken.

In yet another embodiment of the present invention, the organic solvent used is ethyl acetate.

In yet another embodiment of the present invention, the recycled aqueous layer of step (v) is enriched successively with galactose, the overall carbon utilisation efficiency towards its formation being in the range of 26-35% with respect to carbon amount in substrate taken.

In yet another embodiment of the present invention, the KCl content of raw seaweed juice was 3.5-4.2% (w/v) and the juice may be used as is in step (vii) or after concentration.

In yet another embodiment of the present invention, thermal distillation of aqueous stream additionally gives potable water which is passed carbon filter to eliminate any odour.

In yet another embodiment of the present invention, concentration of Ha is 1.0-5.0 M and more specifically 2.25 to 2.75 M.

In yet another embodiment of the present invention, the required HCl is obtained through bipolar electro-dialysis (ED) of seaweed juice or from aqueous phase after recovery of potassium sulphate and with/without the further operation of step (viii).

In yet another embodiment of the present invention, bipolar ED of seaweed juice additionally gives KOH/NaOH which is useful for recovery of magnesium hydroxide from aqueous stream after potassium sulphate recovery.

In yet another embodiment of the present invention, levulinic acid and formic acid are co-produced in 80-85% yield with respect to galactose present.

In yet another embodiment of the present invention, carbon utilisation efficiency of 80-85% for HMF, levulinic acid and formic acid taken together whereas the carbon utilisation is 60-62% for levulinic acid and formic acid production directly from κ-carrageenan.

In yet another embodiment of the present invention, the thermal energy requirement is met through combustion of additional supplies of granular biomass.

In yet another embodiment of the present invention, the electrical energy requirement for bipolar ED and other purposes is also obtainable through gasification of the granular biomass.

In yet another embodiment of the present invention, the combustion or gasification of granule gives additionally $H_2SO_4$ and ash rich in glasserite fertilizer.

In yet another embodiment of the present invention, $Mg(HSO_4)_2$ is prepared through the reaction of $Mg(OH)_2$ and $H_2SO_4$ under autoclave condition at 100-110° C. for 1-3 hours.

In yet another embodiment of the present invention, the yield of pristine κ-carrageenan was 45-55% (w/w), the molecular weight of the repeating polysaccharide unit was 424, the organic carbon content was 32-33% (w/w) sulphate content is 20-22% (w/w) and the potassium content was 6-8%.

In yet another embodiment of the present invention, yield of insoluble residue obtained in step (ii) is 30-33% (w/w) while its calorific value was 14-15 MJ/kg.

In yet another embodiment, the amount of pristine κ-carrageenan charged is 5-10% (w/v) and concentration of bisulphate catalyst is in the range of 0.33-0.63 M in step (iii).

In yet another embodiment of the invention, galactose co-produced in step (iii) was stable under the reaction conditions employed and its concentration rose linearly in the aqueous phase over the cycles.

In yet another embodiment of the process, the water obtained in step (vii) is passed through a carbon filter to eliminate any odour.

In a preferred embodiment of the process, 1.5-2.5 M HCl was used as acid catalyst in levulinic acid synthesis.

In a still more preferred embodiment of the process, solid acid catalyst may be used in the levulinic acid process of step (viii).

In yet another embodiment of the process, HCl required for levulinic acid synthesis may be obtained through bipolar electro-dialysis (ED) of seaweed juice.

In yet another embodiment of the process, bipolar ED of seaweed juice additionally gives KOH/NaOH which is useful for recovery of magnesium hydroxide employed for magnesium bisulphate synthesis as also for neutralization of potassium bisulphate generated during HMF synthesis.

In another embodiment of the process, process energy requirements are met through combustion/gasification of additional supplies of granular biomass, the requirement of such additional granule being 3.35 tonnes per ton of granule processed.

In yet another embodiment, combustion/gasification of granule gave additionally $H_2SO_4$ and ash rich in glasserite fertilizer.

In another embodiment of the process, distillation of organic solvents used in the process may be undertaken using solar thermal energy.

In yet another embodiment, by-product aqueous stream after conducting all operations is blended with surplus juice leading to zero effluent discharge and simultaneous fortification of the juice for foliar spray application.

Detailed Description of the Invention

The biological material used in the present application i.e. seaweed *Kappaphycus alvarezii* is obtained from CSMCRI_Marine algal Research Station (CSIR-MAndapam Campus-623519, Distt. Ramanathapuram, Tamil Nadu) (9°15'N, 78°58'E). The invention relates to an integrated process for the production of fuel intermediates (HMF and levulinic acid), agri-nutrients ($K_2SO_4$, $K_3(NaSO_4)_2$, fortified sea weed juice) and fresh water from fresh *Kappaphycus alvarezii* seaweed. The invention recognised that κ-carrageenan derived from this seaweed has a composition which could serve as a source of biofuels and also a source of potassium sulphate. In targeting the well known fuel intermediate 5-hydroxymethyl furfural, $Mg(HSO4)_2$ was found to give reproducible yields over many cycles albeit with co-formation of galactose. By utilising the galactose, in turn, for synthesis of levulinic acid and formic acid, in essence three important products (HMF, levulinic acid, formic acid) could be obtained in relatively pure forms from κ-carrageenan through stage-wise synthesis. The spent aqueous stream gave potassium sulphate, the key inventive step being use of seaweed juice as co-reactant which provided access to the potassium sulphate field in the Lowenherz phase diagram. The invention is an example of a standalone, self-sustainable bio-refinery which draws on the seaweed biomass for process energy and generates its own catalysts as part of the scheme, with virtually no external inputs other than the fresh seaweed biomass.

Accordingly, an integrated process is disclosed for the production of fuel intermediates, agri-nutrients and potable water from the fresh biomass of *Kappaphycus alvarezii* seaweed comprising:
  (i) expelling of the seaweed juice from the fresh biomass by the known method of mechanically shearing of the seaweed and filtering the resultant slurry to obtain residual biomass and sea weed juice;
  (ii) extraction of pristine κ-carrageenan from residual biomass;
  (iii) treating with aqueous acid catalyst under autoclave condition to obtain 5-hydroxymethyl furfural (HMF), galactose and additional amount of bisulphate as potassium bisulphate generated from the substrate itself;
  (iv) extracting the HMF in pure form with organic solvent and thereafter neutralizing the generated bisulphate in aqueous phase with magnesium hydroxide;
  (v) charging fresh lot of κ-carrageenan into the aqueous phase and repeating the process of step (iii) and continuing in this manner over several cycles using the same organic layer or fresh solvent for HMF extraction;
  (vi) finally neutralizing the aqueous layer to neutral pH with magnesium hydroxide; (vii) adding seaweed juice to shift the equilibrium of the composition of the aqueous phase from schoenite to potassium sulphate and carrying out thermal distillation to recover potassium sulphate in pure form;
  (vii) recovering galactose in pure form by known methods or converting it into ethanol by well known methods or treating the aqueous phase with acid catalyst under autoclave condition to convert galactose into levulinic acid and formic acid;
  (viii) neutralizing the spent aqueous layer, recovering magnesium hydroxide and thereafter fortifying the surplus juice with the nutrient rich aqueous stream.

The term pristine is used for raw material as obtained.

The present invention relates to a self sustainable integrated production of fuel intermediates, agricultural nutrients and pure water from fresh harvest of *Kappaphycus alvarezii* seaweed realizing full potential of the biomass. The novel inventive steps related to the present invention are as follows:
  i. Recognition that the unique composition of κ-carrageenan can be exploited for simultaneous production of fuel intermediates and potassium sulphate.
  ii. Further identifying that acid hydrolysis of sulphated moiety in κ-carrageenan during HMF synthesis would raise the acid concentration of aqueous medium.

iii. Recognising that use of magnesium bisulphate as catalyst along with neutralization of addition bisulphate generated during formation of HMF provides an ideal mechanism through which a constant acid strength can be maintained over large number of cycles.
iv. Recognising further that stage-wise production of HMF followed by levulinic acid and formic acid affords a carbon utilisation efficiency value as high as 82%.
v. Recognising that KCl in the seaweed juice nicely complements the composition of spent aqueous stream after HMF recovery and the two together lead enable $K_2SO_4$ to be produced in pure form with 73% utilisation of sulphate present.
vi. Recognising that process energy can be met from the granule itself which additionally yields glaserite fertilizer and sulphuric acid required for catalyst synthesis.
vii. Recognising that HCl required in levulinic acid synthesis too can be obtained by subjecting the seaweed juice to bipolar electrodialysis while KOH/NaOH produced additionally in a separate compartment can be utilised for magnesium hydroxide synthesis.
viii. Recognising further that the final spent aqueous stream from the integrated process can be blended with surplus seaweed juice to eliminate effluent while fortifying the juice with useful nutrients.

EXAMPLES

Following examples are given by way of illustration therefore should not be construed to limit the scope of the invention.

Example 1

250 g of *K. alvarezii* granules (ca. 8% moisture content) obtained from the fresh seaweed after expelling the seaweed juice mechanically was taken in 5 L seawater and autoclaved at 105° C. and 30 kPa pressure for 60 minutes. The contents were hot centrifuged to obtain 70 g of residue (30.4% yield on dry granule basis) having calorific value of 3473 Kcal/kg. 120 g of pristine κ-carrageenan having ~8% moisture content (48.02% yield w/w) was obtained from the hot aqueous extract through precipitation with IPA (Isopropyl alcohol) (extract: IPA=1:2 v/v). The IPA was distilled from the filtrate and recycled. The moisture content of κ-carrageenan is 8% (w/w). The sulphate content of κ-carrageenan was 21.5% (w/w), the potassium content was 7.7% (w/w). The molecular weight of the repeating unit was 424. The residual mass after recovery of the carrageenan was dried and gave a calorific value of 14.6 MJ/kg with negligible ash formation.

This example teaches the extraction of κ-carrageenan while obtaining a residue useful as solid fuel.

Example 2

1 gm of pristine κ-carrageenan was taken in a conical flask containing 20 ml of 0.1 N $H_2SO_4$ and the mixture was autoclaved at 105° C. for 1 h. The product mixture was shaken thoroughly with equal volume of ethyl acetate and the organic was then subjected to GC-MS. The GC-MS spectra did not show the presence of HMF in the ethyl acetate fraction obtained from the above reaction. Then the acid strength was gradually increased to 0.9 N keeping all other reaction parameter unaltered. The highest yield of HMF (291 mg, 49% carbon utilisation on κ-carrageenan basis) was obtained with 0.3 N $H_2SO_4$ (Table-1).

TABLE 1

Data on yield and selectivity of HMF formation from κ-carrageenan in autoclave as a function of $H_2SO_4$ concentration

| 1 | Amount of feed (κ-carrageenan) taken g/(mmol) | Catalyst $H_2SO_4$ (N) | Solvent $H_2O$ (mL) | HMF (% of carbon utilisation) | Selectivity of HMF in organic part (%)[a] |
|---|---|---|---|---|---|
| 1 | 1/(2.36) | 0.1 | 20 | NR | NR |
| 2 | 1/(2.36) | 0.2 | 20 | <20 | low |
| 3 | 1/(2.36) | 0.3 | 20 | 49 | 100 |
| 4 | 1/(2.36) | 0.5 | 20 | 41 | 68 |
| 5 | 1/(2.36) | 0.7 | 20 | 34 | 54 |
| 6 | 1/(2.36) | 0.9 | 20 | 30 | 50 |

[a]GC selectivity

The above experiment was repeated with 10 g of κ-carrageenan using 0.3 N $H_2SO_4$. The aqueous layer was extracted with ethyl acetate (1:1) and the layer was saved. Further, in the above acidic aqueous layer, 10 g κ-carrageenan was added and hydrolysed under same conditions described above followed by extraction with ethyl acetate. The cycle was repeated for 6 times. After 6 cycles the ethyl acetate fractions were analysed individually. The HMF yield rose in the second cycle and then remained steady till the fifth cycle. Beyond this, the yield and selectivity dropped markedly.

This example teaches that when $H_2SO_4$ was used as the acid catalyst, acid strength of 0.3 N was optimum and further recycling of aqueous phase up to 6 times was feasible.

Example 3

The reaction of Example 2 was repeated using $Mg(HSO_4)_2$ as catalyst. The data are presented in Table 2 below.

TABLE 2

Data on yield and selectivity of HMF formation from κ-carrageenan in autoclave as a function of $Mg(HSO_4)_2$ concentration.

| Entry | Amount of feed (κ-carrageenan) taken g/(mmol) | Solvent $H_2O$ (mL) | Catalyst $Mg(HSO_4)_2$ (M) | HMF (% of carbon utilisation) | Selectivity of HMF in organic part (%)[a] |
|---|---|---|---|---|---|
| 1 | 2.5/(5.9) | 50 | 0.33 | NR | NR |
| 2 | 2.5/(5.9) | 50 | 0.38 | 25.5 | 99 |
| 3 | 2.5/(5.9) | 50 | 0.43 | 32.8 | 99 |
| 4 | 2.5/(5.9) | 50 | 0.48 | 42.3 | 99 |
| 5 | 5/(11.8) | 100 | 0.48 | 43 | 99 |
| 6 | 5/(11.8) | 100 | 0.53 | 31 | 80 |
| 7 | 5/(11.8) | 100 | 0.63 | 27 | 78 |

[a]GC selectivity 10 g of κ-carrageenan was taken in 200 mL of 0.48 M $Mg(HSO_4)_2$ (optimized condition) and autoclaved at 105° C. for 1 h. The product mixture was extracted with ethyl acetate. $KHSO_4$ (3.21 g; 23.6 mmol) released during hydrolysis of κ-carrageenan was neutralized with $Mg(OH)_2$ (0.68 g, 11.8 mmol) and thereafter the aqueous phase recycled as in Example 2. 10 such cycles, each with 10 g of κ-carrageenan was feasible and 36.05 g of HMF having 92% purity by HPLC assay was obtained. Galactose was co-produced in the reaction and its concentration built up steadily over the cycles as shown in FIG. 1. The total amount of galactose in the aqueous stream was estimated to be 20.84 g through HPLC assay.

This example teaches that when $Mg(HSO_4)_2$ was used as the acid catalyst, and additional acid generated in the process was neutralized with $Mg(OH)_2$ to maintain a constant acid strength throughout, HMF and galactose could be obtained with a total carbon utilisation efficiency of 88% with respect to carbon content in the κ-carrageenan taken. The example further teaches that through this approach HMF was obtained in pure isolated form whereas galactose was obtained as an aqueous solution.

Example 4

The experiment of Example 3 with 0.48 M $Mg(HSO_4)_2$ was repeated over 6 cycles with 20 g of κ-carrageenan per cycle. 42.5 g of HMF was isolated in a yield similar to that in Example 3. The aqueous phase after 6 cycles measuring 250 mL was neutralized with $Mg(OH)_2$. The galactose content was estimated to be 26.9 g. The inorganic constituents in the aqueous phase after neutralization were as follows: $K^+$, 6.9 g; $Mg^{2+}$, 10.2 g; $SO_4^{2-}$, 50.6 g. The concentrations expressed in the form of $K_2SO_4$ and $MgSO_4$ were 8.42 and 42.05 mol per 1000 mol of $H_2O$. Into this solution 1.8 L of seaweed juice containing 4.14% (w/v) KCl was added and the contents subjected to progressive evaporation in a rotavap to recover $K_2SO_4$ in pure form. 66.8 g $K_2SO_4$ (73% yield on sulphate basis) was obtained. Additionally, 1.5 L of fresh water was collected which, after treatment through carbon filter, was free of any odour, and had a pH value of 7.1 and 80 mg·$L^{-1}$ total dissolved solids.

This example teaches the recovery of potassium sulphate and distilled water as co-products, together with HMF and galactose, from κ-carrageenan using the seaweed juice as co-reactant.

Example 5

The neutralized aqueous stream generated after 10 cycles in Example 3 was desulphated using $CaCl_2$. 160 mL filtrate containing 20.84 g of galactose was taken and acidified with concentrated HCl to an acid strength of 2.5 M HCl and then reacted in an autoclave under similar conditions adopted for HMF synthesis. 11.06 g of levulinic acid and 4.06 g of formic acid was found to be present (HPLC assay) in the aqueous layer with overall carbon utilisation efficiency of 81.3% with respect to galactose.

This example teaches the further conversion of galactose derived in the course of HMF synthesis from κ-carrageenan into levulinic acid and formic acid, with overall carbon utilisation towards HMF, levulinic acid and formic acid being 82% on the basis of carbon content in κ-carrageenan taken.

Example 6

The residual mass from Example 4 after separation of $K_2SO_4$ was reacted as in Example 5. 11.2 g of levulinic acid was obtained in the organic layer.

This example teaches the synthesis of levulinic acid and formic acid from galactose after $K_2SO_4$.

Example 7

20 g of pristine κ-carrageenan of Example 1 was taken in 200 mL of 2.5 M HCl and was reacted under autoclave condition at 105° C. for 1 h. After reaction the aqueous layer was found to contain 6.39 g of levulinic acid and 2.36 g of formic acid (HPLC assay) in nearly similar proportion.

This example teaches the production of levulinic acid and formic acid directly from κ-carrageenan but the carbon utilisation was only 62.7% compared to the value of 82% in Example 5.

Example 8

10 g of dry granule after washing was taken in alumina porcelain and was combusted at 800° C. in a tubular furnace for 3 hours under continuous air flow. The flue gas generated during combustion was bubbled through 800 ml distilled water. The pH of the resultant solution was 2.6 and the acid strength was found to be 0.0067 N through titration. $CO_3^{2-}$, $SO_4^{2-}$ and $Cl^-$ were not detected in any substantial amount but after treatment of the solution with $H_2O_2$ (20% v/v of 30% vol $O_2$) followed by stirring at room temperature for 30 min, $SO_4^{2-}$ was detected by $BaCl_2$ test, indicating that the acidic solution formed from the flue gas was $H_2SO_3$. The $SO_4^{2-}$ amount was estimated to be 0.032% (w/v), i.e., 0.256 g $SO_4^{2-}$ from the 10 g of granule taken.

This example teaches the production of sulphuric acid from raw granule of *Kappaphycus alvarezii* after expelling of the juice.

Example 9

Raw granule of *Kappaphycus alvarezii* was washed and dried and 10 g of dry granule was taken in crucible and combusted at 550° C. for 4 hour in presence of air. Ash was obtained in 22% (w/w) yield and weight percentages of K, Na and $SO_4^{2-}$ were 37.3%, 5.9% and 55.6%, respectively, while the chloride amount was negligible. Its powder XRD (FIG. 2) revealed a mixed composition of $K_3Na(SO_4)_2$ (glaserite) and $K_2SO_4$.

This example teaches the production of a second solid potash fertilizer from *Kappaphycus alvarezii*.

Example 10

Figure 2:
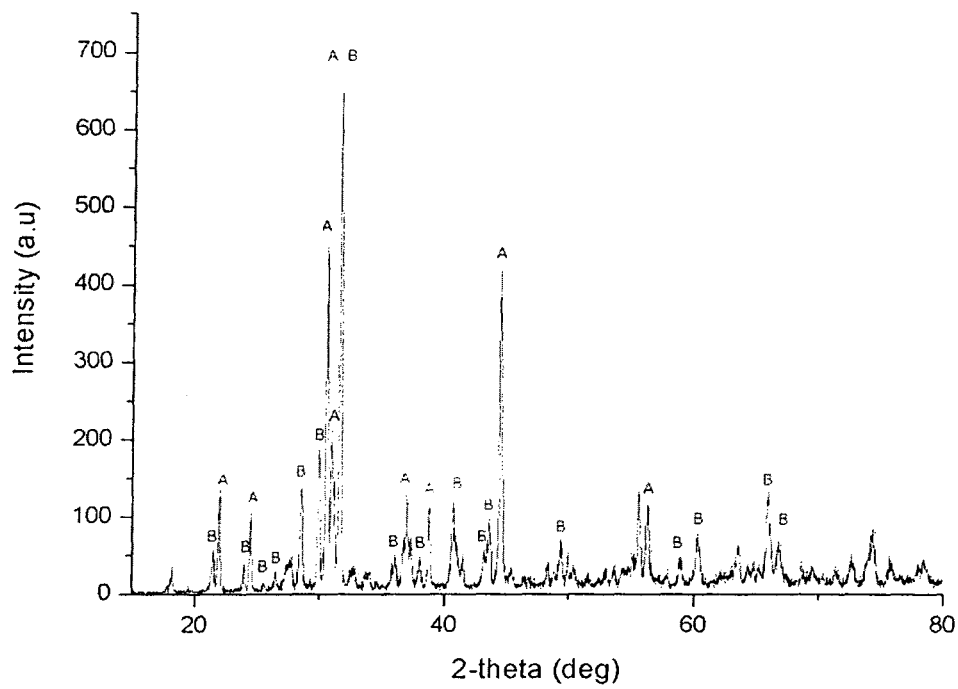
FIG. 2 represents powder XRD of potash rich fertilizer (two principal phases were glaserite [$K_3Na(SO_4)_2$] (A) and $K_2SO_4$ (B)) in the form of ash obtained after combustion of dry granules at 550° C. Search match analysis was performed with high score plus software using ICDD-JCPDF data base (International Centre for Diffraction Data—Joint Committee on Powder Diffraction Standard).
Figure 3:
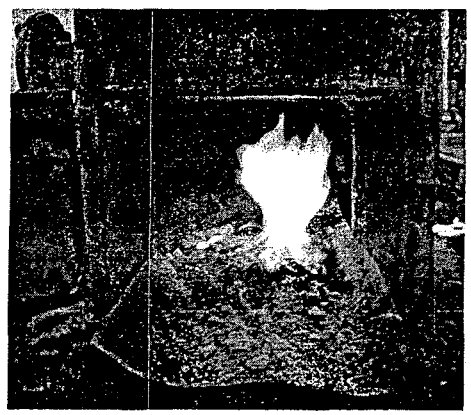
FIG. 3 represents combustion of granules in a solid fuel fired boiler.

Granule of Example 9, having calorific value of 11.87 MJ/kg was charged into a solid fuel fired boiler and its combustion could be sustained as shown in FIG. 2 This example teaches the potential to generate thermal energy from granule to meet the process energy requirement for practice of the examples above. It is computed that for every 1 tonne of granule processed, 3.35 tonne of raw granule would be required for this purpose. Besides producing energy the granule would yield sulphuric acid and glaserite fertilizer as disclosed in Examples 8-9.

Example 11

38 kg of washed and dried granule similar to the one used in Example 9 was fed to a fixed bed downdraft gasifier intermittently over 1.5 h. To initialize the gasification 1.52 kg of wood pieces were charged at the start. The gas having composition of 1.47% carbon monoxide, 1.09% methane and 6.64% hydrogen (at around 12:50 h) burnt with a sustained yellowish flame during the entire period. The gas after clean up can be fed to a 100% producer gas engine to generate power.

This example teaches the potential to generate electricity besides thermal energy from granule.

Example 12

Bipolar Electrodialysis (ED) of Sap Solution for Generation of HCl and KOH from KCl Rich Seaweed Juice Bipolar ED was conducted in a homemade ED stack assembled with 5 cell triplets consisting of monopolar interpolymer cation- and anion-exchange membranes and bipolar membrane. The effective surface area of a single membrane was 80 cm². The experiments were conducted with 700 mL of sap containing 4.1% w/v (0.55 M) KCl. The sap was circulated continuously in the electrodialyser between bipolar membrane and cation-exchange membrane (forming alkali stream) and between anion-exchange membrane and bipolar membrane (forming acid stream). A DC electrical potential (40 V) was applied between the two electrodes by an AC-DC rectifier having variable current capacity. Samples of acid and alkali streams were collected at regular intervals and analysed by acid-base titration. After 4.5 h the experiment was terminated. 440 mL of 0.42 M HCl and 390 mL of 0.44 M KOH was obtained.

This example teaches the use of seaweed juice to produce HCl and KOH required in the integrated process.

ADVANTAGES OF THE INVENTION

Distillation of organic solvents, where required, may be undertaken using solar thermal energy also.

Thermal energy requirement is met through combustion of additional supplies of granular biomass.

Electrical energy requirement for bipolar ED and other purposes is also obtainable through gasification of the granular biomass.

Combustion or gasification of granule gives additionally $H_2SO_4$ and ash rich in glasserite fertilizer.

The invention claimed is:

1. An integrated process for the production of fuel intermediates, agri-nutrients and potable water from *Kappaphycus alvarezii* seaweed comprising the steps of:
   i. of mechanically shearing *Kappaphycus alvarezii* seaweed to obtain a slurry, and filtering the slurry to separate a first solid residual biomass from a first aqueous phase;
   ii. mixing the first solid residual with seawater and incubating at 105° C.-120° C. at a pressure of 25 to 35 kPa for 50 to 70 minutes, then centrifuging to obtain an a second solid insoluble residue and a second aqueous phase, mixing the second aqueous phase with isopropyl alcohol and centrifuging to obtain κ-carrageenan as a solid;
   iii. suspending the κ-carrageenan solid at 5-10% (w/v) in an aqueous solution containing an acid catalyst and incubating at 100-110° C. for 1-3 hours at 25-30 kPa to obtain a third aqueous phase comprising 5-hydroxymethyl furfural (HMF), galactose and potassium bisulphate;
   iv. mixing the third aqueous phase with an organic solvent to obtain an organic phase containing HMF and a fourth aqueous phase, separating said organic phase from the fourth aqueous phase and extracting HMF from the organic phase to obtain recycled organic solvent;
   v. optionally suspending additional κ-carrageenan solid into the fourth aqueous phase and repeating the process of step (iii), and repeating step (iv) with the recycled organic solvent;
   vi. adding magnesium hydroxide to the fourth aqueous phase in an amount sufficient to achieve pH-neutral fourth aqueous phase;
   vii. adding the first aqueous phase to the pH-neutral fourth aqueous phase to produce a fifth aqueous phase, and subjecting the fifth aqueous phase to evaporative concentration to obtain crystals of potassium sulphate and a sixth aqueous phase containing galactose;
   viii. subjecting the sixth aqueous phase to further processing selected from (a) concentrating through evaporation to obtain crystals of galactose and a seventh aqueous phase (b) fermenting to obtain ethanol and a seventh aqueous phase or (c) adding dilute aqueous acid and incubating at 100-110° C. for 1-3hours at 25-30 kPa to obtain a levulinic acid and formic acid and a seventh aqueous phase;
   ix. neutralizing the seventh aqueous phase and recovering magnesium hydroxide.

2. The process of claim 1, wherein in step (ii) the yield of the κ-carrageenan is 45-55% by weight according to the weight of the first aqueous phase and the yield of the second solid insoluble residue is 30-35% by weight according to the weight of the first aqueous phase.

3. The process of claim 1, wherein in step (iii) the acid catalyst is $Mg(HSO_4)_2$ or $H_2SO_4$.

4. The process of claim 3, wherein the acid catalyst is $Mg(HSO_4)_2$ at a concentration of 0.33-0.63 M.

5. The process of claim 1, wherein the 5-hydroxymethyl furfural (HMF) obtained in step (iii) contain 25-70% of the carbon in the κ-carrageenan.

6. The process of claim 1, wherein in step (iv) the organic solvent is ethyl acetate.

7. The process of claim 1, wherein in step (vii) the first aqueous phase has a KCl content of 3.5-4.2% (w/v).

8. The process of claim 1, wherein water is condensed from them evaporative concentration in step (vii), wherein the water is passed through a carbon filter to eliminate odour.

9. The process of claim 1, wherein in step (viii)(c) the dilute aqueous acid is HCl and the concentration of HCl is 1.0-5.0 M.

10. The process of claim 1, further wherein the first aqueous phase or the seventh aqueous phase is further subjected to bipolar electro-dialysis (ED) to obtain HCl.

11. The process of claim 10, wherein the bipolar ED of the first aqueous phase additionally gives KOH/NaOH.

12. The process of claim 1, wherein in step (viii)(c) the yield of the levulinic acid and formic acid are together 80-85% by weight of the galactose.

13. The process of claim 1, wherein in step (viii) the yield of HMF, levulinic acid and/or formic acid together contain 80-85% of the carbon in the κ-carrageenan.

14. The process of claim 1, further comprising combusting or gasifying the first solid residual biomass to generate energy.

15. The process of claim 14 wherein the combustion or gasification further generates $H_2SO_4$ and ash containing glasserite.

* * * * *